United States Patent
Chang

(10) Patent No.: US 11,602,668 B2
(45) Date of Patent: Mar. 14, 2023

(54) SYSTEM AND METHOD FOR MOTION ANALYSIS

(71) Applicant: IMOTEK Inc., Taipei (TW)

(72) Inventor: Ching-Wei Chang, Taipei (TW)

(73) Assignee: IMOTEK, INC., Taipei (TW)

( * ) Notice: Subject to any disclaimer, the term of this patent is extended or adjusted under 35 U.S.C. 154(b) by 1118 days.

(21) Appl. No.: 16/228,842

(22) Filed: Dec. 21, 2018

(65) Prior Publication Data

US 2019/0192908 A1   Jun. 27, 2019

(30) Foreign Application Priority Data

Dec. 26, 2017   (TW) .................................. 106145657

(51) Int. Cl.
| | | |
|---|---|---|
| *A63B 69/16* | (2006.01) | |
| *G01P 13/04* | (2006.01) | |
| *G06V 40/20* | (2022.01) | |
| *A63B 24/00* | (2006.01) | |
| *A61B 5/11* | (2006.01) | |

(52) U.S. Cl.
CPC ........ *A63B 24/0062* (2013.01); *A61B 5/1116* (2013.01); *A61B 5/1122* (2013.01); *A63B 69/16* (2013.01); *G01P 13/04* (2013.01); *G06V 40/20* (2022.01); *A63B 2024/0068* (2013.01); *A63B 2220/803* (2013.01); *A63B 2220/836* (2013.01); *A63B 2225/20* (2013.01); *A63B 2225/52* (2013.01)

(58) Field of Classification Search
CPC ................ A63B 24/0062; A63B 69/16; A63B 2024/0068; A63B 2220/803; A63B 2225/20; A61B 5/1116; A61B 5/1122; G01P 13/04; G06V 40/20
See application file for complete search history.

(56) References Cited

U.S. PATENT DOCUMENTS

| | | | |
|---|---|---|---|
| 9,381,417 B2 * | 7/2016 | Inoue ..................... | A63B 69/16 |
| 2007/0142177 A1 * | 6/2007 | Simms ................. | A61B 5/1127 |
| | | | 482/8 |
| 2015/0116472 A1 * | 4/2015 | Li ........................... | A43D 1/02 |
| | | | 348/77 |

FOREIGN PATENT DOCUMENTS

| | | |
|---|---|---|
| EP | 2865330 A1 | 4/2015 |
| TW | 201118627 A1 | 6/2011 |
| TW | 201515635 A | 5/2015 |

OTHER PUBLICATIONS

Extended European Search Report for European Application No. 18215231.4, dated Apr. 11, 2019.
Taiwanese Search Report for Taiwanese Application No. 106145657, dated Aug. 31, 2018, with English translation.

* cited by examiner

*Primary Examiner* — Mohamed Charioui
(74) *Attorney, Agent, or Firm* — Birch, Stewart, Kolasch & Birch, LLP

(57) ABSTRACT

A system for motion analysis includes a sensing device positioned at a knee joint of a bicycle rider, and an electronic device in communication with the sensing device. The electronic device is configured to receive, from the sensing device, a series of pieces of sensed data representing orientations of the sensing device at different times, to determine a motion trajectory of a knee of the rider based on the received pieces of sensed data, and to generate an estimation result regarding correctness of a riding posture of the rider based on the motion trajectory.

10 Claims, 10 Drawing Sheets

SYSTEM AND METHOD FOR MOTION ANALYSIS

CROSS-REFERENCE TO RELATED APPLICATION

This application claims priority of Taiwanese Invention Patent Application No. 106145657, filed on Dec. 26, 2017.

FIELD

The disclosure relates to motion analysis.

BACKGROUND

Bicycle riding is considered to be a good leisure activity. However, bicycle riding with a bad posture may harm the knee/ankle joint(s) of the rider. For example, a riding posture that involves too much knee rotation and/or abduction may induce anterior knee pain. Besides, the deformity or illness of the lower limbs (e.g., genu valgum or genu varum) may cause a bad riding posture.

Ideally, when riding a bicycle with a normal (or good) posture, the moving track of each of the knees of the rider should approximate a figure-eight shape or a narrow ellipse with its longitudinal axis substantially perpendicular to the ground when observed along the bicycle. An example of the moving track with a good posture is illustrated in FIG. 1. In contrast, an abnormal (or bad) riding posture would render the ellipse of the moving track wider or render the eight-figure shape of the moving track skewed. An example of the moving track with a bad posture is illustrated in FIG. 2. A conventional bike fitting method first captures, with at least one camera, moving tracks of multiple markers (e.g., LED markers) attached on a user when the user is riding a bicycle that is fixed at a spot, and then estimates the riding posture of the user by analyzing the moving tracks of the markers using a computing device. Such conventional bike fitting method requires complex and costly equipments. Moreover, the conventional bike fitting method is inapplicable to analysis of riding postures under various real-world environments because it can only be performed indoors.

SUMMARY

Therefore, an object of the disclosure is to provide a method and a system for motion analysis that can alleviate at least one of the drawbacks of the prior art.

According to the disclosure, the method is to be implemented by an electronic device in communication with a sensing device over a communication network, wherein the sensing device is positioned at a knee joint of a bicycle rider. The method includes: receiving, from the sensing device, a series of pieces of sensed data generated by the sensing device according to movement of the knee joint during a time period of bicycle riding, each of the pieces of sensed data corresponding to a time point within the time period and including a set of three values representing an orientation of the sensing device with respect to a fixed coordinate system; determining a trajectory formed by a plurality of data points each of which corresponds to a respective one of the pieces of sensed data, and each of which has coordinates defined by predetermined two elements of the set of three values, the trajectory including at least one loop; and generating an estimation result regarding correctness of a riding posture of the rider based on the at least one loop of the trajectory.

According to the disclosure, the system includes a sensing device that is to be positioned at a knee joint of a bicycle rider. The sensing device includes a case, and a communication unit and a sensing unit accommodated in the case that are electrically connected to each other. The sensing unit is configured to generate a series of pieces of sensed data according to movement of the knee joint during a time period of bicycle riding, wherein each of the pieces of sensed data corresponds to a time point within the time period and includes a set of three values representing an orientation of the case with respect to a fixed coordinate system. The system further includes an electronic device capable of communication with the sensing device over a communication network. The electronic device includes a communication module and a processing module electrically connected with the communication module. The communication module is configured to communicate with the communication unit of the sensing device over the communication network. The electronic device is configured to receive the series of the pieces of sensed data from the sensing device, and to determine a trajectory that includes at least one loop and that is formed by a plurality of data points each of which corresponds to a respective one of the pieces of sensed data, and each of which has coordinates defined by predetermined two elements of the set of three values. The electronic device is further configured to generate an estimation result regarding correctness of a riding posture of the rider based on the at least one loop of the trajectory.

BRIEF DESCRIPTION OF THE DRAWINGS

Other features and advantages of the disclosure will become apparent in the following detailed description of the embodiment (s) with reference to the accompanying drawings, of which.

DETAILED DESCRIPTION

Figure 1:
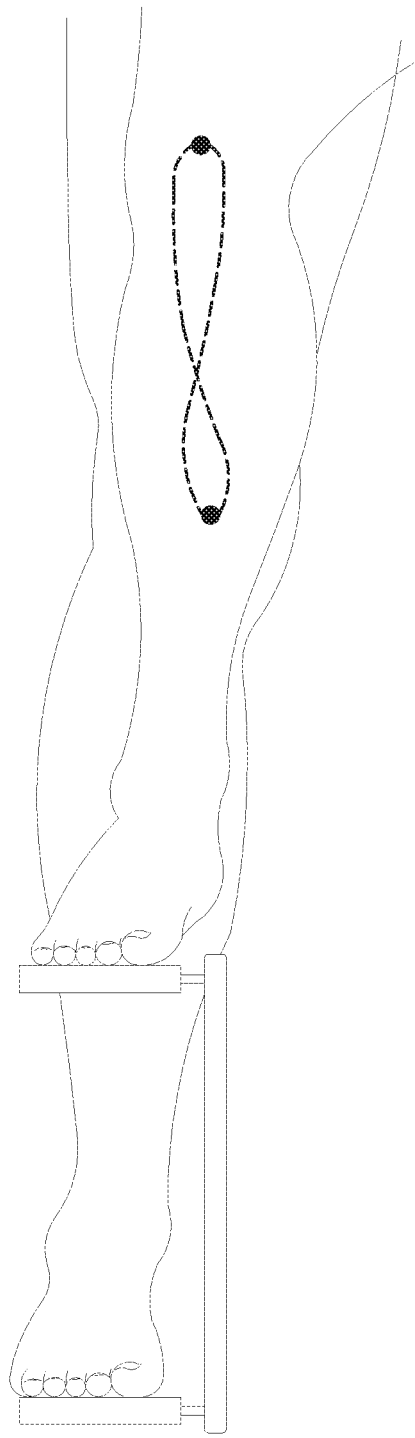
FIG. 1 is a schematic view of a moving track of a knee of a rider with a good riding posture.
Figure 2:
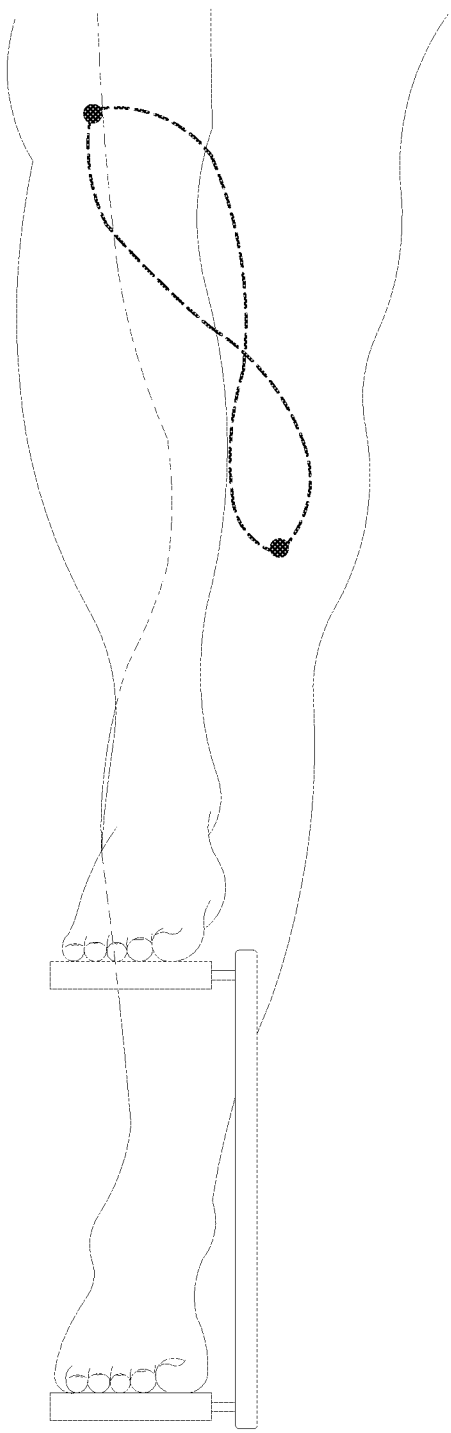
FIG. 2 is a schematic view of a moving track of a knee of a rider with a bad riding posture.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 3:
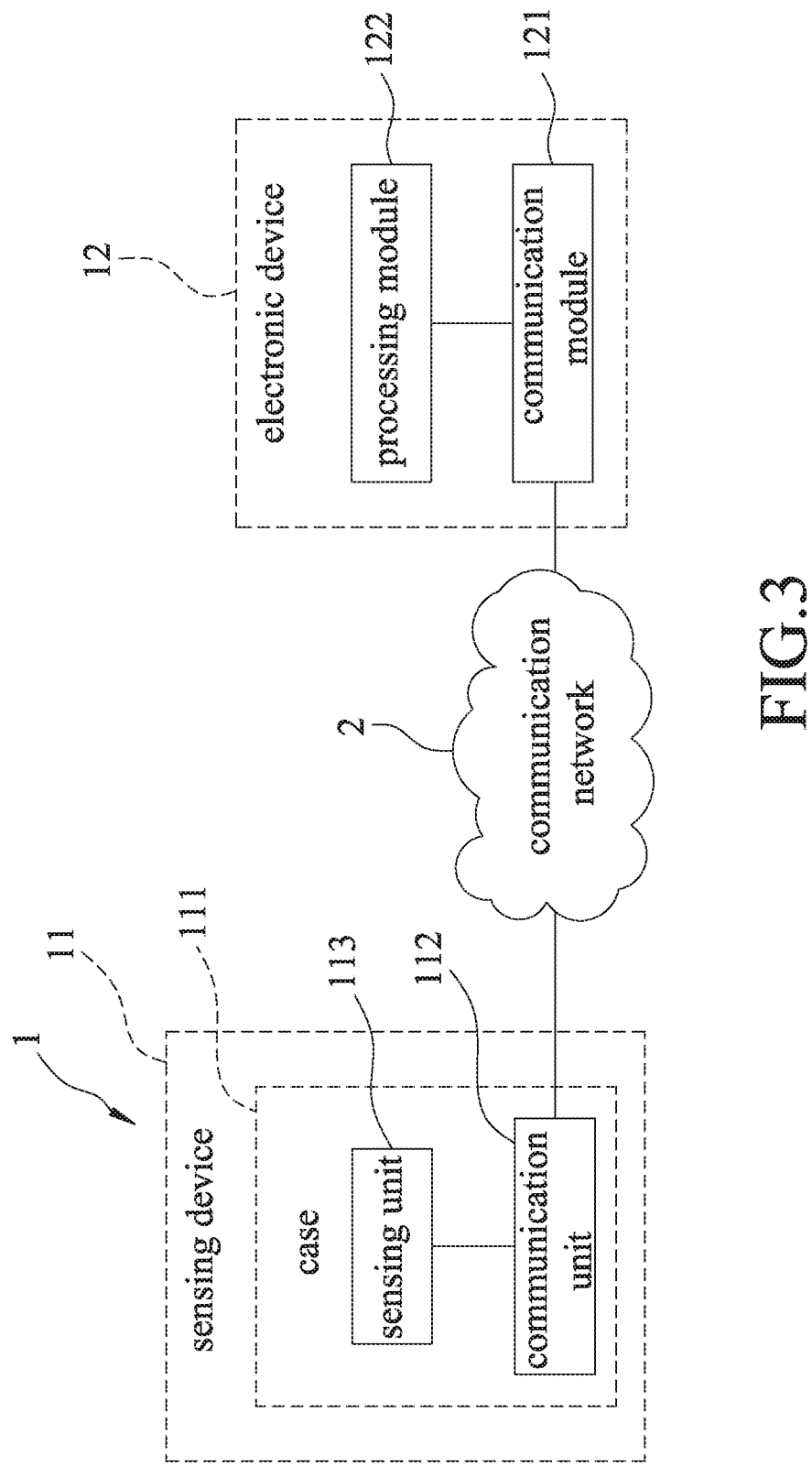
FIG. 3 is a block diagram which exemplarily illustrates a system for motion analysis according to an embodiment.

FIG. 3 is a block diagram which exemplarily illustrates a system 1 for motion analysis according to an embodiment of this disclosure. Referring to FIG. 3, the system 1 includes a sensing device 11 and an electronic device 12 that may communicate with the sensing device 11 over a communication network 2. In an embodiment, the communication network 2 is a Bluetooth network, but the disclosure is not limited thereto.

According to an embodiment, the sensing device 11 includes a case 111, and a communication unit 112 and a sensing unit 113 accommodated in the case 111. The communication unit 112 and the sensing unit 113 are electrically connected to each other. According to an embodiment, the sensing device 11 is configured to be positioned at a knee joint of a user.

Figure 4:
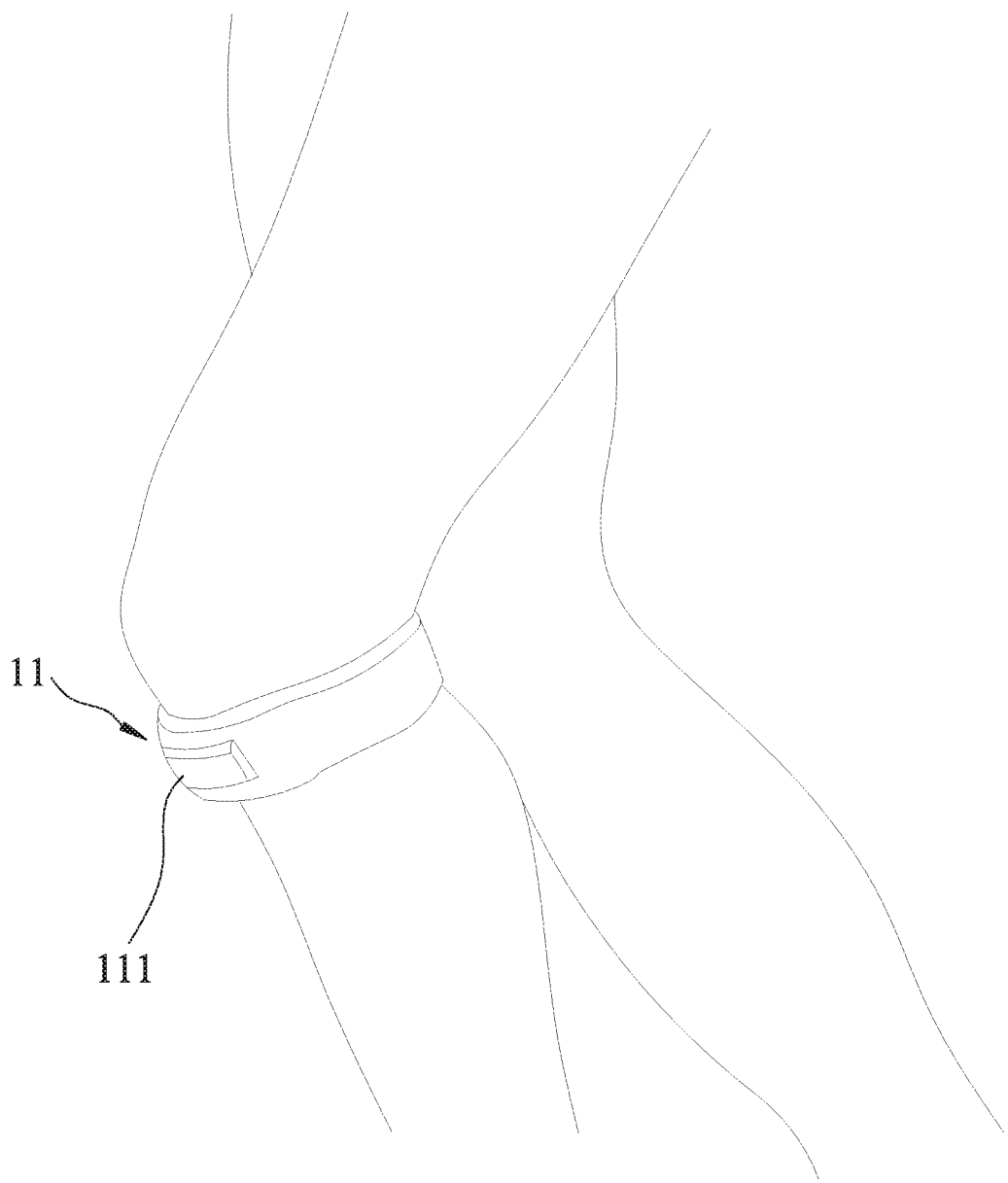
FIG. 4 is a schematic view of an exemplary wearing position of a sensing device for motion analysis according to an embodiment.

As illustrated in FIG. 4, the sensing device 11 may further include a strap attached to the case 111 to allow the sensing device 11 to be fastened to the knee joint. In an embodiment, the sensing device 11 is suggested to be positioned at the tibial tuberosity of the user. The position of the tibial tuberosity can be found with bare hands. For example, when the user intends to wear the sensing device 11 on the left knee, the user may first sit on a chair and then repeatedly bend his/her left knee while touching the front of the left knee with the right hand in order to find the patella. After locating the patella, the user may close his/her index, middle and ring fingers of the right hand together, and put them below the patella along the surface of the left knee with the upper edge of the index finger aligned with the bottom edge of the patella. In this situation, the tibial tuberosity would be right below the ring finger, and that is where the sensing device 11 should be worn.

According to an embodiment, the sensing unit 113 is configured to generate a series of pieces of sensed data according to movement of the knee joint during a time period of bicycle riding, wherein each of the pieces of sensed data corresponds to a time point within the time period and includes a set of three values representing an orientation of the case 111 with respect to a fixed coordinate system. The fixed coordinate system may be a coordinate system that is defined by the three anatomical planes or axes (i.e., the sagittal, coronal and transverse planes, or the sagittal, frontal and longitudinal axes) of the user's body. The three values may respectively represent angle measurements (in degrees) of three kinds of movements of the knee joint, i.e., flexion/extension in the sagittal plane, abduction/adduction in the coronal plane and rotation around the longitudinal axis (or the leg bone). According to some embodiments, the three values may be three Euler angle values or three elements of a quaternion that are measured by, for example, an inertial measurement unit (IMU). In this embodiment, the communication unit 112 is exemplified by a Bluetooth chipset, but other communication technologies may be adopted to implement the same, such as WiFi, Zigbee, etc. The sensing unit 113 is exemplified by an IMU which uses a combination of an accelerometer and a gyroscope, and the combination may further include a magnetometer and/or a Global Positioning System (GPS) tracking unit in other embodiments.

Figure 5:
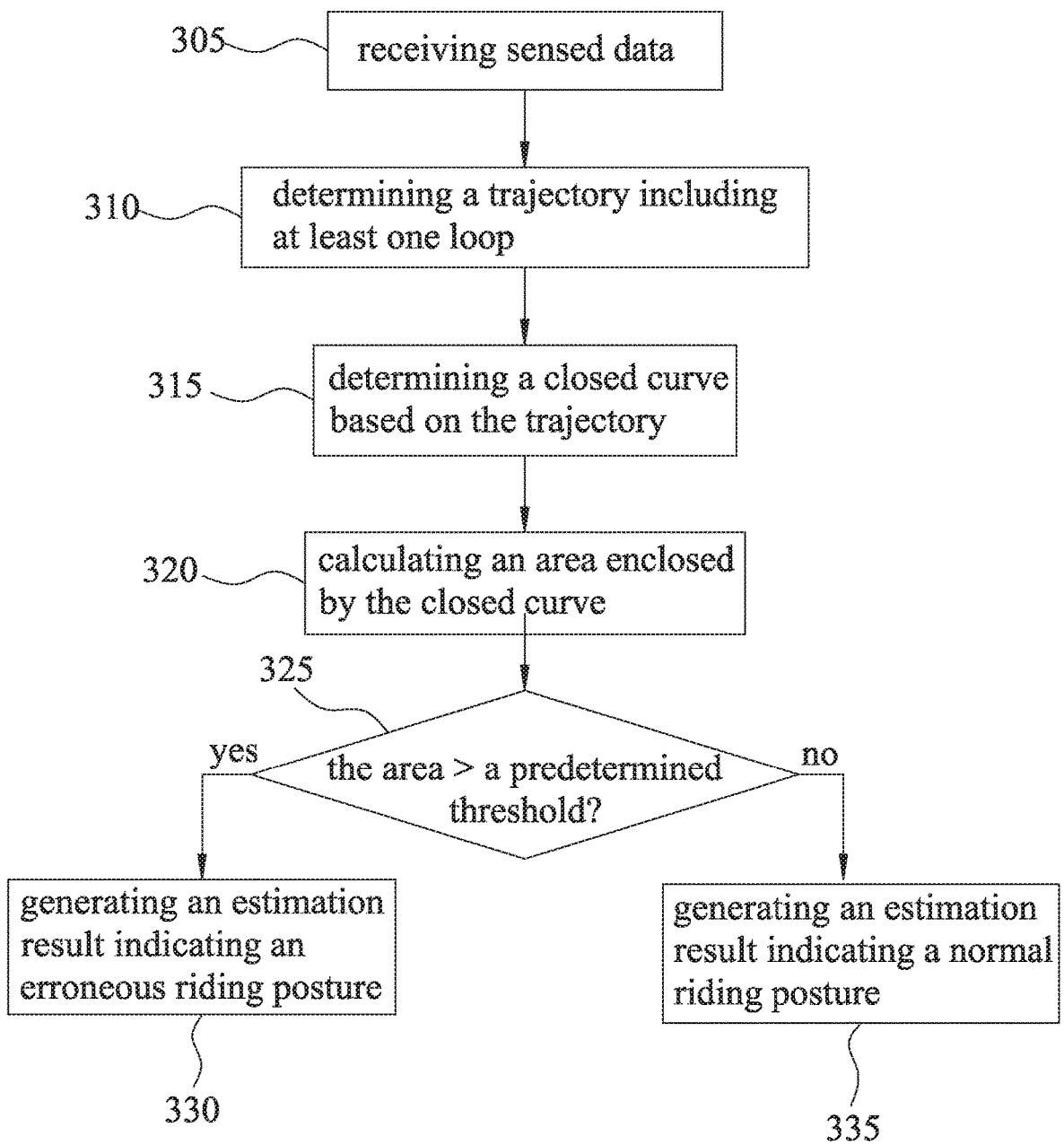
FIG. 5 is a flow chart which illustrates a first exemplary implementation of a method for motion analysis according to an embodiment.
Figure 9:
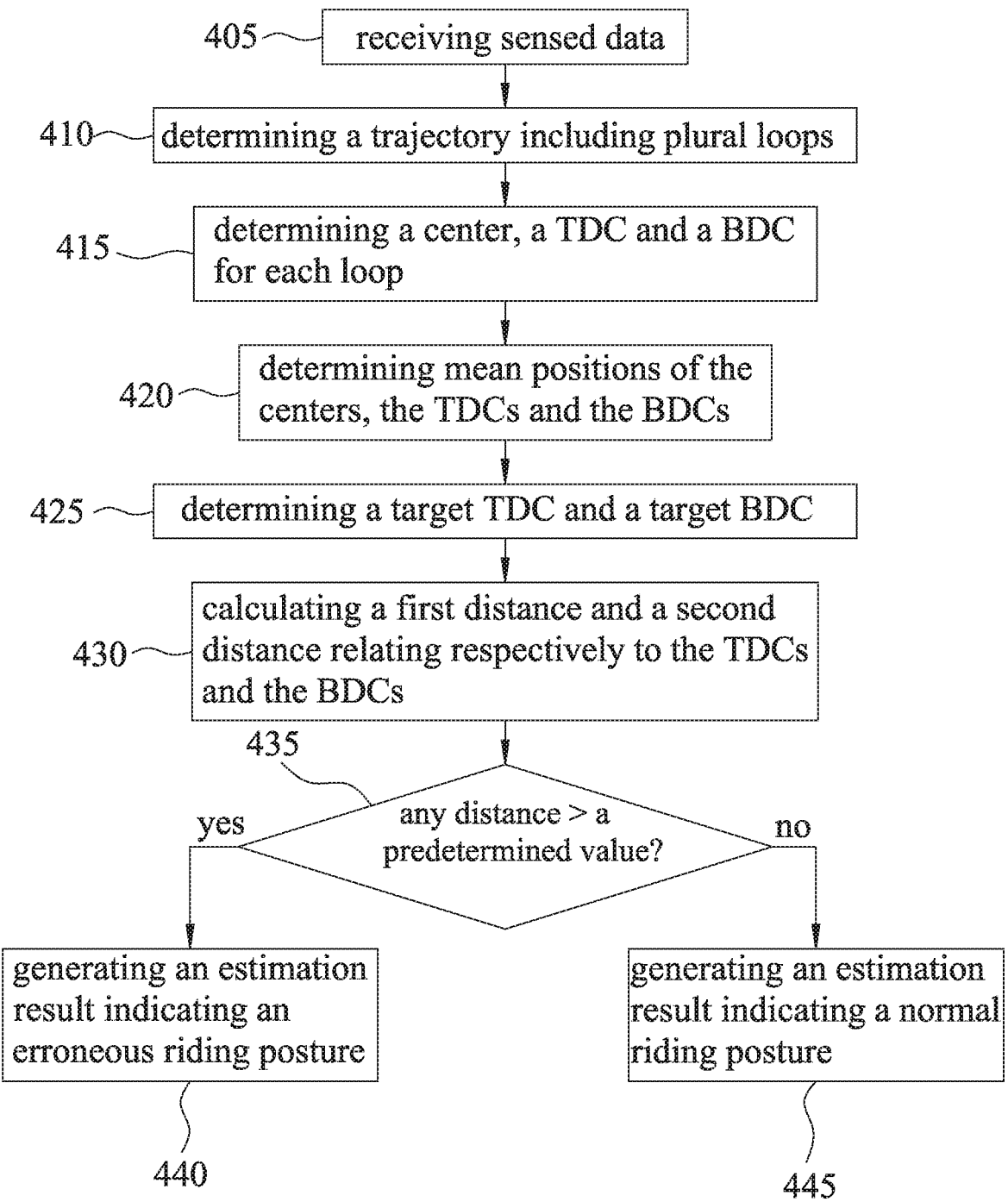
FIG. 9 is a flow chart which illustrates a second exemplary implementation of a method for motion analysis according to an embodiment.

According to an embodiment, the electronic device 12 may be a mobile device that includes a communication module 121 and a processing module 122 that are electrically connected to each other. The communication module 121 is configured to communicate with the communication unit 112 over the communication network 2. According to an embodiment, the processing module 122 is configured to receive the sensed data related to the user from the sensing device 11 through the communication module 121, and to generate an estimation result regarding the correctness of a riding posture of the user based on the received sensed data by performing a method for motion analysis as illustrated in FIG. 5 or 9. Derailed operations of the electronic device 12 will be described below. In this embodiment, the communication module 121 is exemplified by a Bluetooth chipset, but other communication technologies may be adopted to implement the same, such as WiFi, Zigbee, etc. The processing module 122 may be exemplified by a processor, a central processing unit (CPU), a digital signal processor (DSP), a system on a chip (SoC) or any other device having computation capability.

Reference is now made to FIG. 5 which illustrates a first exemplary implementation of the method. In step 305, the electronic device 12 receives, from the sensing device 11, a series of pieces of sensed data generated by the sensing device 11 according to movement of a knee joint of a user wearing the sensing device 11 during a time period of bicycle riding. As mentioned above, each of the pieces of sensed data corresponds to a time point within the time period and includes a set of three values, e.g., three Euler angle values.

Figure 6:
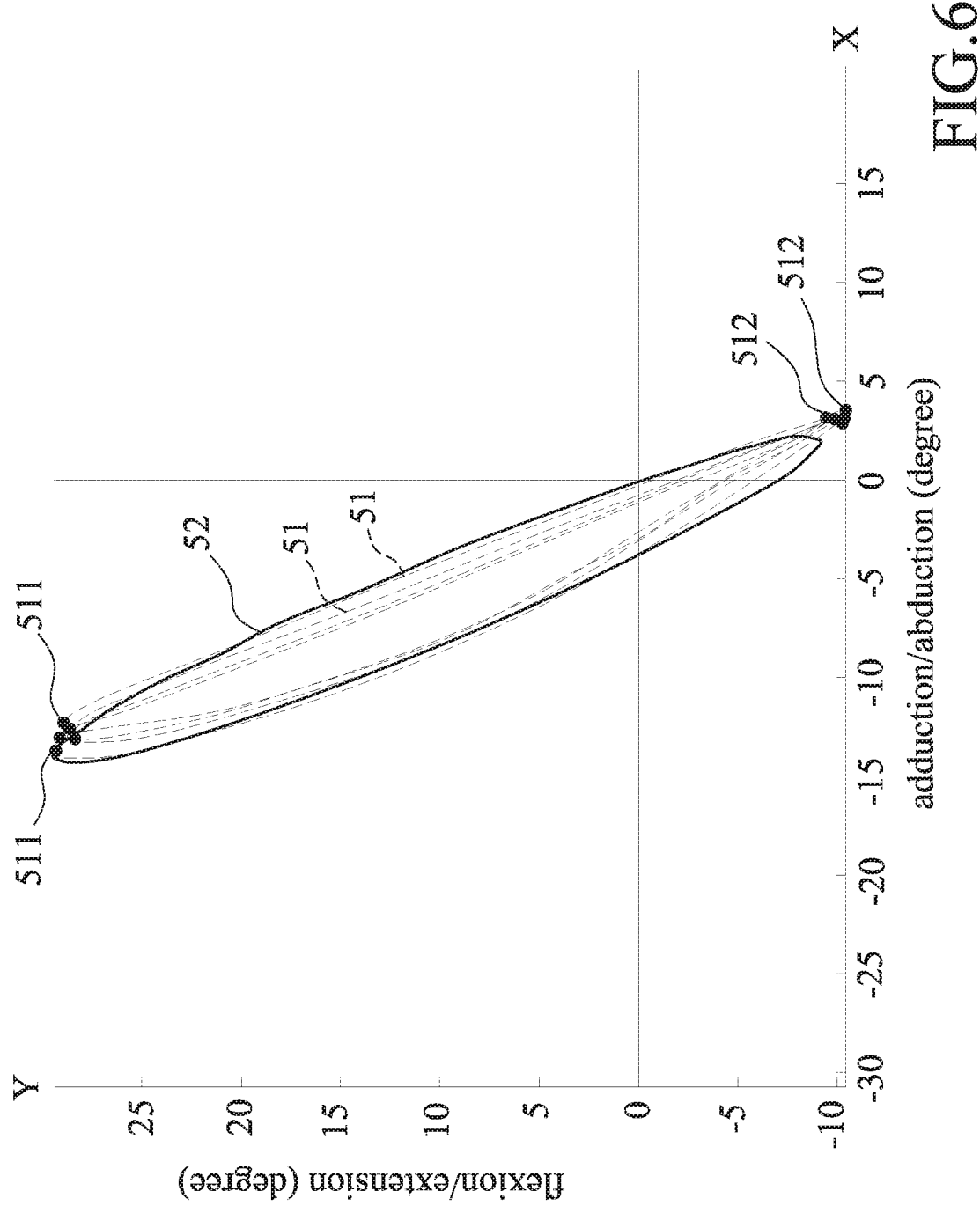
FIGS. 6-8 are coordinate diagrams each illustrating an exemplary trajectory of a motion of a knee joint.
Figure 7:
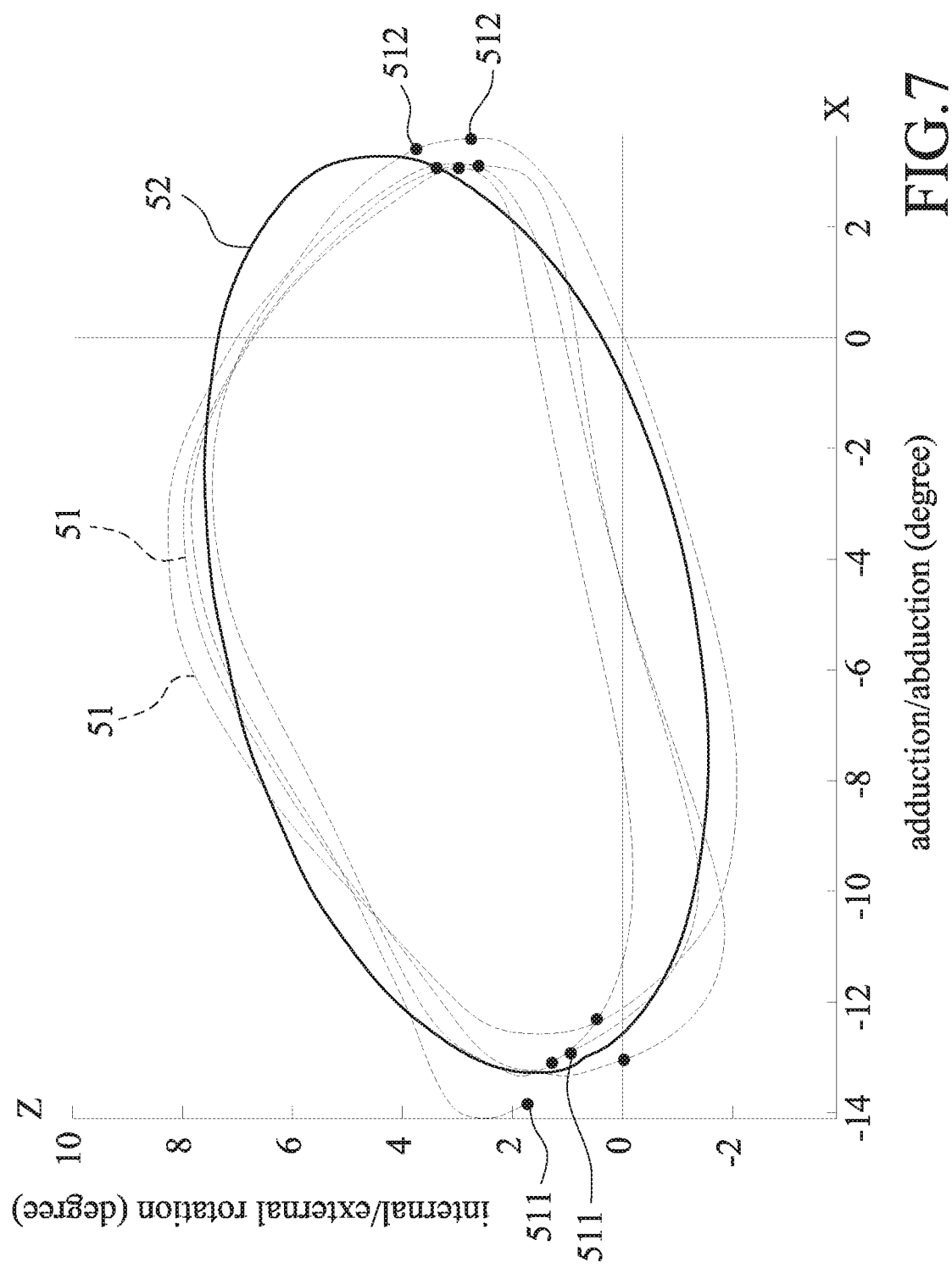
Figure 8:
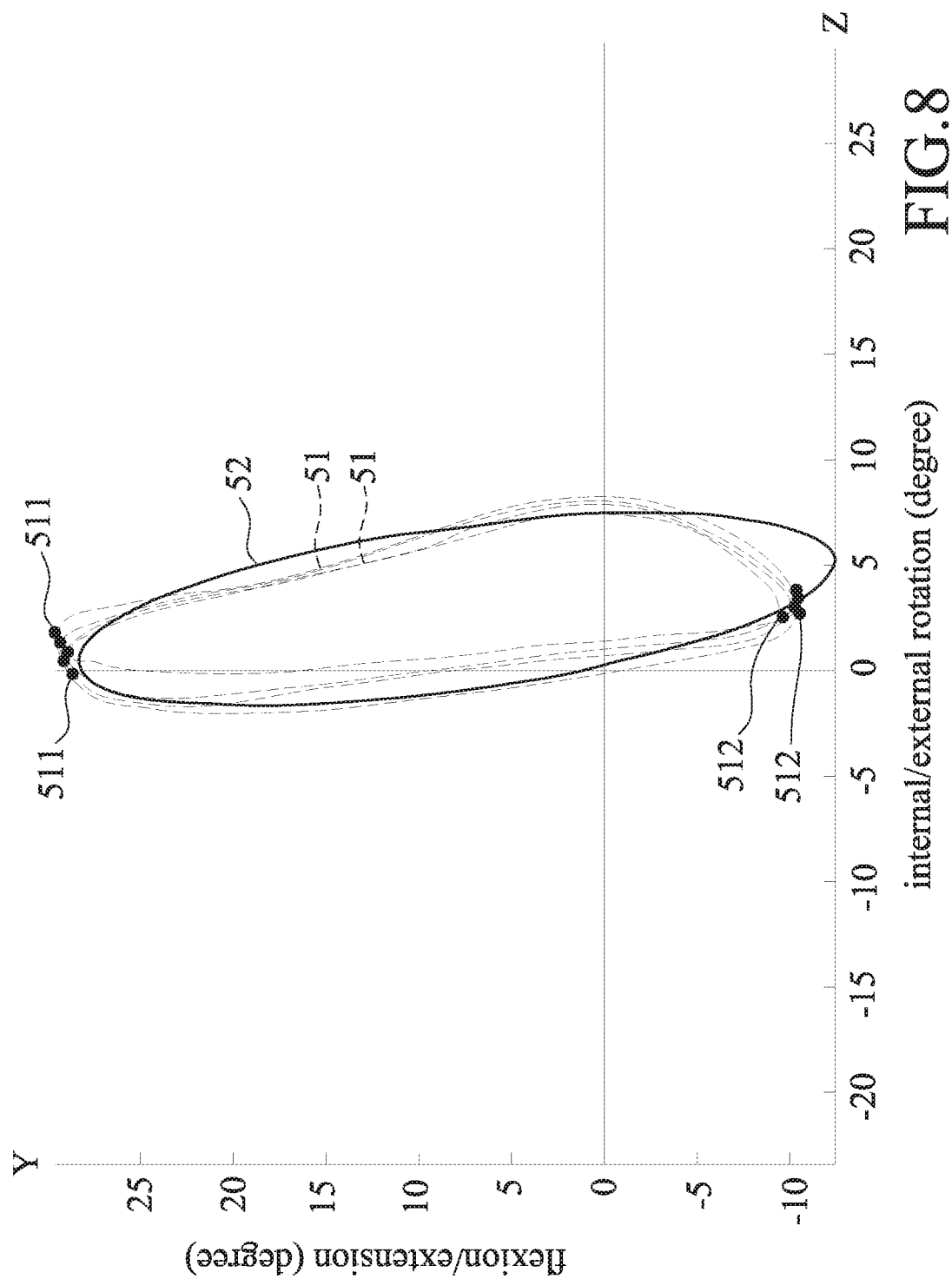

In step 310, the electronic device 12 determines a trajectory including at least one loop. The trajectory is formed by a plurality of data points, each of which corresponds to a respective one of the pieces of sensed data, and each of which has coordinates defined by predetermined two elements of the set of three values included in the respective one of the pieces of sensed data. Since the determination of the trajectory only utilizes two out of three elements of the set of values, three different kinds of trajectories may be derived from the same pieces of sensed data, and the determined trajectory may be any one of them. FIGS. 6-8 exemplarily illustrate the three trajectories (in dotted lines) that are derived from the same pieces of sensed data, where each set of three values is composed of a first element that is representative of the angle measurement (in degrees) of adduction/abduction of the knee joint, a second element that is representative of the angle measurement (in degrees) of flexion/extension of the knee joint and a third element that is representative of the angle measurement (in degrees) of internal/external rotation of the knee joint, and the trajectories of FIGS. 6-8 are plotted respectively according to the first and second elements, the first and third elements, and the second and third elements. As illustrated, the trajectories of FIGS. 6-8 have four loops 51 each.

In an embodiment, the determining the trajectory in step 310 includes determining each of the at least one loop (e.g., the loops 51 in FIGS. 6-8). Each of the loop(s) is formed by a starting data point, an ending data point and at least one middle data point. The first one of the loop(s) may be determined by setting the first data point corresponding to the first (i.e., earliest) one of the pieces of sensed data as the starting data point of the loop, and setting a later data point, assuming it is the $N^{th}$ ($N \geq 3$) data point corresponding to the $N^{th}$ piece of sensed data (in the order of time), as the ending data point of the loop, wherein the distance between the $N^{th}$ data point and the starting data point is smaller than the distance between the $N-1^{th}$ data point and the starting data point and smaller than a predetermined threshold. The at least one middle data point of the first loop includes each data point between the first data point and the $N^{th}$ data point. The second or other subsequent loop (if any) may be determined in a similar way, wherein the starting data point thereof is set to be the data point right after the ending data point of its immediately previous loop. In reality, each loop means one cycle of the crank of the bicycle (i.e., a full circle the user has pedaled).

In step 315, the electronic device 12 determines a closed curve (e.g., the closed curves 52 in FIGS. 6-8) resembling the at least one loop of the trajectory by using principal components analysis (PCA). In an embodiment, the closed curve thus determined is of a fixed shape, for example, an ellipse.

In step 320, the electronic device 12 calculates an area enclosed by the closed curve. The area enclosed by the closed curve may be calculated by integration or by formulas. For example, in an embodiment where the closed curve has the shape of an ellipse, a formula of $A=\pi ab$ may be applied, wherein A denotes the area of the ellipse, and a and b denote the lengths of the semi-major and semi-minor axes, respectively.

It is found by experiment that the areas enclosed by the closed curves derived from wrong riding postures (whether caused by a bad riding habit or illness) are greater than those derived from right riding postures. Therefore, in step 325, the electronic device 12 determines whether the calculated area enclosed by the closed curve is greater than a predetermined threshold. When it is determined that the calculated area enclosed by the closed curve is greater than the predetermined threshold, the process proceeds to step 330 where the electronic device 12 generates an estimation result indicating an erroneous riding posture of the user. Otherwise, when it is determined that the calculated area enclosed by the closed curve is not greater than the predetermined threshold, the process proceeds to step 335 where the electronic device 12 generates an estimation result indicating a normal riding posture of the user. The estimation result may be for medical use, such as injury treatment of injured knee/ankle joints or preventive treatment of riding-posture correction.

According to an embodiment, the method of FIG. 5 may further include, after step 310 and before step 325, a step of determining, by the electronic device 12, a crank rotational speed (also known as cadence which is the number of revolutions of the crank per minute (RPM)) of the bicycle based on a total number of the loop(s) of the trajectory determined in step 310 and a length of the time period. In this case, the estimation results generated in steps 330 and 335 may include information about the crank rotational speed.

FIG. 9 illustrates a second exemplary implementation of the method for motion analysis that may be performed by the electronic device 12 of the system 1 of FIG. 1.

Referring to FIG. 9, in step 405 which is analogous to step 305 of FIG. 5, the electronic device 12 receives, from the sensing device 11, a series of pieces of sensed data generated by the sensing device 11 according to movement of a knee joint of a user during a time period of bicycle riding, where each of the pieces of sensed data corresponds to a time point within the time period and includes a set of three values, e.g., three Euler angle values.

In step 410 which is similar to step 310 of FIG. 5, the electronic device 12 determines a trajectory that is formed by a plurality of data points. Each of the data points corresponds to a respective one of the received pieces of sensed data, and has coordinates defined by predetermined two elements of the set of three values included in the respective one of the received pieces of sensed data. The trajectory includes plural loops which may be determined as discussed above with respect to step 310.

In step 415, the electronic device 12 determines, for each of the loops of the trajectory, a center (e.g., a geometric center) of the loop, a top dead center (TDC) (e.g., TDCs 511 in FIGS. 6-8) which is a point on the loop that is farthest from the center, and a bottom dead center (BDC) (e.g., BDCs 512 in FIGS. 6-8) which is a farthest point from the center on a part of the loop opposite to the other part of the loop on which the TDC is located.

In step 420, the electronic device 12 derives a mean position of the centers of the loops, a mean position of the TDCs of the loops, and a mean position of the BDCs of the loops.

In step 425, the electronic device 12 selects a target TDC from among the TDCs and a target BDC from among the BDCs of the loops. The target TDC is one of the TDCs that is farthest from the mean position of the centers of the loops, and the target BDC is one of the BDCs that is farthest from the mean position of the centers of the loops.

In step 430, the electronic device 12 calculates a first distance between the target TDC and the mean position of the TDCs of the loops and a second distance between the target BDC and the mean position of the BDCs of the loops.

It is found by experiment that at least one of these two distances derived from a wrong riding posture would be greater than that/those derived from a right riding posture. Therefore, in step 435, the electronic device 12 determines whether any of the first and second distances exceeds a predetermined value. If so, the process proceeds to step 440 where the electronic device 12 generates an estimation result indicating an erroneous riding posture of the user. Otherwise, the process proceeds to step 445 where the electronic device 12 generates an estimation result indicating a normal riding posture of the user.

According to an embodiment, the method of FIG. 9 may further include, after step 410 and before step 435, a step of determining, by the electronic device 12, a crank rotational speed of the bicycle based on a length of the time period and a total number of the loops, a total number of the TDCs of the loops or a total number of the BDCs of the loops, and the estimation results generated in steps 440 and 445 may include information about the crank rotational speed.

Figure 10:
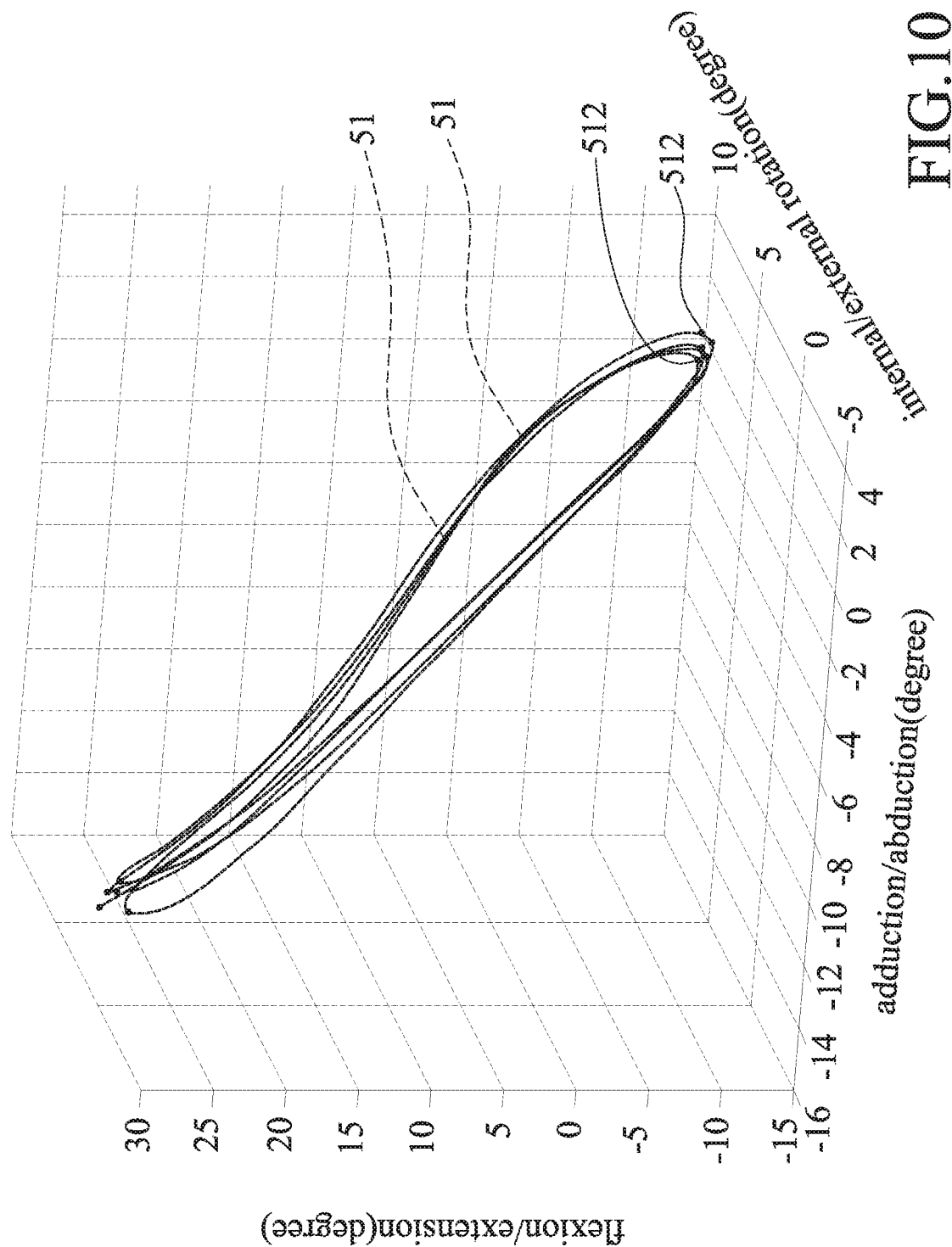
FIG. 10 is a coordinate diagram illustrating another exemplary trajectory of a motion of a knee joint.

Modifications may be made to the methods of FIGS. 5 and 9. For example, the trajectory determined in step 310 or step 410 may be formed by loop(s) that utilize/utilizes all three, instead of only two, elements of the set of three values. An example of such trajectory is illustrated in FIG. 10.

A beneficial characteristic of the present disclosure is that the disclosed method for motion analysis needs basically only two devices (i.e., the sensing device 11 and the electronic device 12), and thus may remarkably reduce the cost and the complexity of equipment in comparison to conventional techniques. Further, due to simplicity and portability of the needed equipment, the disclosed method can be performed not only indoors but also outdoors, and thus has a wider range of applications. Another beneficial characteristic of the present disclosure is that, the disclosed system and method may conveniently obtain, without any extra tools, the crank rotational speed that is useful in determining the physical fitness or health status of the user.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for motion analysis that is to be implemented by an electronic device in communication with a sensing device over a communication network, the sensing device being positioned at a knee joint of a rider of a bicycle, the method comprising:
   receiving, from the sensing device, a series of pieces of sensed data generated by the sensing device according to movement of the knee joint during a time period of bicycle riding, each of the pieces of sensed data corresponding to a time point within the time period and including a set of three values representing an orientation of the sensing device with respect to a fixed coordinate system;
   determining a trajectory formed by a plurality of data points each of which corresponds to a respective one of the pieces of sensed data, and each of which has coordinates defined by predetermined two elements of the set of three values, the trajectory including multiple loops;
   determining, for each of the loops of the trajectory, a center of the loop, a top dead center (TDC) which is a point on the loop that is farthest from the center, and a bottom dead center (BDC) which is a farthest point from the center on a part of the loop opposite to the other part of the loop on which the TDC is located;
   deriving a mean position of the centers of the loops, a mean position of the TDCs of the loops, and a mean position of the BDCs of the loops;
   selecting a target TDC from among the TDCs of the loops that is farthest from the mean position of the centers of the loops;
   selecting a target BDC from among the BDCs of the loops that is farthest from the mean position of the centers of the loops; and
   generating an estimation result regarding correctness of a riding posture of the rider based on the mean position of the TDCs of the loops, the mean position of the BDCs of the loops, the target TDC, the target BDC and a predetermined value.

2. The method of claim 1, further comprising:
   determining a closed curve resembling the loops of the trajectory by using principal components analysis (PCA); and
   calculating an area enclosed by the closed curve; wherein the generating an estimation result includes generating the estimation result based on comparison of the area to a predetermined threshold.

3. The method of claim 2, wherein the generating an estimation result includes:
   generating an estimation result indicating an erroneous riding posture when the area enclosed by the closed curve is greater than the predetermined threshold; and
   generating an estimation result indicating a normal riding posture when the area enclosed by the closed curve is not greater than the predetermined threshold.

4. The method of claim 1, wherein the generating an estimation result includes:
   generating an estimation result indicating an erroneous riding posture when one of a distance between the target TDC and the mean position of the TDCs of the loops, and a distance between the target BDC and the mean position of the BDCs of the loops exceeds the predetermined value; and
   generating an estimation result indicating a normal riding posture when none of the distance between the target TDC and the mean position of the TDCs of the loops and the distance between the target BDC and the mean position of the BDCs of the loops exceeds the predetermined value.

5. The method of claim 1, further comprising:
   determining a crank rotational speed of the bicycle, based on a length of the time period and a total number of one of the TDCs and the BDCs of the loops.

6. A system for motion analysis, comprising:
   a sensing device to be positioned at a knee joint of a rider of a bicycle, said sensing device including:
      a case,
      a communication unit accommodated in said case, and
      a sensing unit accommodated in said case and electrically connected with said communication unit, said sensing unit being configured to generate a series of pieces of sensed data according to movement of the knee joint during a time period of bicycle riding, each of the pieces of sensed data corresponding to a time point within the time period and including a set of three values representing an orientation of said case with respect to a fixed coordinate system; and
   an electronic device capable of communication with said sensing device over a communication network, said electronic device including:
      a communication module configured to communicate with said communication unit of said sensing device over the communication network, and
      a processing module electrically connected with said communication module, said processing module being configured to
         receive the series of the pieces of sensed data from said sensing device, determine a trajectory formed by a plurality of data points each of which corresponds to a respective one of the pieces of sensed data, and each of which has coordinates defined by predetermined two elements of the set of three values, the trajectory including multiple loops,
         determine, for each of the loops of the trajectory, a center of the loop, a top dead center (TDC) which is a point on the loop that is farthest from the center, and a bottom dead center (BDC) which is a farthest point from the center on a part of the loop opposite to the other part of the loop on which the TDC is located,
         derive a mean position of the centers of the loops, a mean position of the TDCs of the loops, and a mean position of the BDCs of the loops,
         select a target TDC from among the TDCs of the loops that is farthest from the mean position of the centers of the loops,
         select a target BDC from among the BDCs of the loops that is farthest from the mean position of the centers of the loops, and generate an estimation result regarding correctness of a riding posture of the rider based on the mean position of the TDCs of the loops, the mean position of the BDCs of the loops, the target TDC, the target BDC and a predetermined value.

7. The system of claim 6, wherein said processing module is further configured to:
determine a closed curve resembling the loops of the trajectory by using principal components analysis (PCA);
calculate an area enclosed by the closed curve; and
generate the estimation result based on comparison of the area to a predetermined threshold.

8. The system of claim 7, wherein said processing module is further configure to generate an estimation result indicating an erroneous riding posture when the area enclosed by the closed curve is greater than the predetermined threshold, and to generate an estimation result indicating a normal riding posture when the area enclosed by the closed curve is not greater than the predetermined threshold.

9. The system of claim 6, wherein said processing module is further configured to:
generate an estimation result indicating an erroneous riding posture when one of a distance between the target TDC and the mean position of the TDCs of the loops, and a distance between the target BDC and the mean position of the BDCs of the loops exceeds the predetermined value; and
generate an estimation result indicating a normal riding posture when none of the distance between the target TDC and the mean position of the TDCs of the loops and the distance between the target BDC and the mean position of the BDCs of the loops exceeds the predetermined value.

10. The system of claim 6, wherein said processing module is further configured to determine a crank rotational speed of the bicycle, based on a length of the time period and a total number of one of the TDCs and the BDCs of the loops.

\* \* \* \* \*